United States Patent
Urch et al.

(10) Patent No.: US 6,294,545 B1
(45) Date of Patent: Sep. 25, 2001

(54) BICYCLIC AMINES AND THEIR USE AS INSECTICIDES

(75) Inventors: Christopher John Urch; Roger Salmon, both of Bracknell (GB)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 09/554,423

(22) PCT Filed: Oct. 15, 1998

(86) PCT No.: PCT/GB98/03098

§ 371 Date: May 12, 2000

§ 102(e) Date: May 12, 2000

(87) PCT Pub. No.: WO99/26478

PCT Pub. Date: Jun. 3, 1999

(30) Foreign Application Priority Data

Nov. 21, 1997 (GB) .................................................. 9724693

(51) Int. Cl.⁷ ........................ A61K 31/439; C07D 401/04
(52) U.S. Cl. .................. 514/278; 514/299; 514/304; 546/18; 546/21; 546/112; 424/265.1
(58) Field of Search .............................. 546/18, 94, 124, 546/112, 21; 514/299, 304, 278; 424/265.1

(56) References Cited

U.S. PATENT DOCUMENTS 5,859,024 * 1/1999 Hotson et al. ..................... 514/299
5,922,732 * 7/1999 Urch et al. ......................... 514/304

FOREIGN PATENT DOCUMENTS

| 2 301 819 A | 12/1996 | (GB) . |
| 96/37494 | 11/1996 | (WO) . |
| 97/43286 | 11/1997 | (WO) . |

* cited by examiner

Primary Examiner—Alan L. Rotman
Assistant Examiner—Rita Desai

(57) ABSTRACT

A compound of formula (I) wherein A is a bidentate group of the formula: XC=CY or XCH—CHY (wherein X and Y are independently hydrogen, hydroxy, acyloxy, alkoxy, cyano or halogen); and Ar is optionally substituted phenyl or optionally substituted heteroaryl; or an acid addition salt, quaternary ammonium salt or N-oxide derived therefrom; provided that when A is $CH_2$—$H_2$ then Ar is neither 5-chloropyrid-3-yl nor 5-trifluoromethylpyrid-3-yl; an insecticidal, acaricidal or nematicidal composition comprising an insecticidally, acaricidally or nematicidally effective amount of a compound of formula (I); a method of using a compound of formula (I) to combat or control insect, acarine or nematode pests; and processes for preparing a compound of said formula.

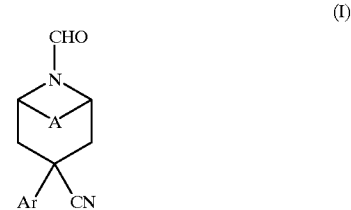

(I)

10 Claims, No Drawings

BICYCLIC AMINES AND THEIR USE AS INSECTICIDES

This is a 371 of Application No. PCT/GB98/03098, filed Oct. 15, 1998.

This invention relates to bicyclic amine derivatives, to processes for preparing them, to insecticidal compositions comprising them and to methods of using them to combat and control insect pests.

Insecticidal bicyclic amines are disclosed in WO 96/37494.

The present invention provides a compound of formula (I):

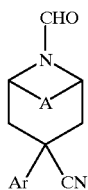

wherein A is a bidentate group of formula XC=CY or XCH—CHY (wherein X and Y are independently hydrogen, hydroxy, acyloxy, alkoxy, cyano or halogen); and Ar is optionally substituted phenyl or optionally substituted heteroaryl; or an acid addition salt, quaternary ammonium salt or N-oxide derived therefrom; provided that when A is $CH_2$—$CH_2$ then Ar is neither 5-chloropyrid-3-yl nor 5-trifluoromethylpyrid-3-yl.

It will be appreciated that the compounds of formula (I) are capable of existing in more than one isomeric form since groups may be positioned in either an exo or endo relationship, and the present invention embraces within its scope both exo and endo forms and mixtures thereof in all proportions and also any further isomeric variants arising from cis and trans substitution patterns or chiral centres.

Heteroaryl includes 5- and 6-membered rings comprising one, two or three heteroatoms selected form the group comprising nitrogen, oxygen and sulphur, said rings being optionally fused to a benzene ring. Examples of heteroaryl are pyridine, pyrazine, pyridazine, pirimidine, pyrrole, pyrazole, imidazole, 1,2,3- and 1,2,4-triazoles, furan, thiophene, oxazole, isoxazole, thiazole, isothiazole, 1,2,3- and 1,3,4-oxadiazoles, 1,2,3- and 1,3,4-thiadiazoles, benzoxazole, indole, benzofuran, benzothiophen and benzimidazole.

Halogen includes fluorine, chlorine, bromine and iodine.

Alkyl moieties preferably contain from 1 to 6, more preferably from 1 to 4, carbon atoms. They can be in the form of straight or branched chains, for example methyl, ethyl, n- or iso-propyl, or n-, sec-, iso- or tert-butyl.

Acyloxy is preferably alkylcarbonyloxy or optionally substituted phenylcarbonyloxy. Acyloxy is, for example, acetyloxy or benzoyloxy.

Phenyl and heteroaryl rings are preferably optionally substituted with: halogen, hydroxy, mercapto, $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy, halo($C_{1-4}$)alkyl (for example $CF_3$), halo($C_{1-4}$) alkoxy (for example $OCF_3$), $C_{1-4}$alkylthio, halo($C_{,1-4}$)alkylthio, hydroxy($C_{1-4}$)alkyl, $C_{1-4}$alkoxy($C_{1-4}$)alkyl (for example $CH_3OCH_2$), $C_{3-6}$cycloalkyl (such as cyclopentyl or cyclohexyl), $C_{3-6}$cycloalkyl($C_{1-4}$)alkyl (such as cyclopentylmethyl or 1-cyclopropyleth-1-yl), phenyl, phenoxy, $SF_5$, cyano, thiocyanato, nitro, —NR'R", —NHCOR', —CONR'R", —COOR', —SOR', —$SO_2$R', —$SO_2$($C_{3-6}$) alkenyl, —$OSO_2$R', —$NHSO_2$R', —$SO_2$NR'R", —COR', —CR'=N", —CR'=NOR" or —N=CR'N"; two substituents, when they are in adjacent positions on the phenyl or heteroaryl ring can join to form a fused aliphatic ring (especially to form a fused 6-membered carbon aliphatic ring) or a fused alkylenedioxy ring (such as methylenedioxy or difluoromethylenedioxy); R' and R" are independently hydrogen, $C_{1-4}$alkyl, $C_{1-4}$alkoxy, $C_{1-4}$alkylthio, $C_{3-6}$cycloalkyl, $C_{3-6}$cycloalkyl($C_{1-4}$)alkyl, phenyl or benzyl; the phenyl, phenoxy and benzyl groups being optionally substituted with halogen, $C_{1-4}$alkyl, halo($C_{1-4}$)alkyl, $C_{1-4}$alkoxy or $C_{1-4}$haloalkoxy.

Alkenyl and alkynyl moieties can be in the form of straight or branched chains, and alkenyl moieties can be of either (E)- or (Z)-configuration. Examples are vinyl, allyl and propargyl.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

In one aspect the present invention provides a compound of formula (I) wherein A is $CH_2$—$CH_2$ or CH=CH.

In a further aspect the present invention provides a compound of formula (I) wherein A is CH=CH.

In another aspect the present invention provides a compound of formula (I), wherein Ar is phenyl or pyrazinyl, all being optionally substituted with halogen (especially fluorine, chlorine or bromine), $C_{1-4}$alkyl (especially methyl), $C_{1-4}$alkoxy (especially methoxy), $C_{2-4}$alkenyl, $C_{2-4}$alkynyl or cyano.

In a further aspect the present invention provides a compound of formula (I) wherein Ar is pyridinyl optionally substituted with fluorine, bromine, cyano, $C_{1-4}$alkyl, $C_{1-4}$alkoxy or $C_{2-4}$haloalkyl (such as 2,2,2-trifluoroethyl, 2,2-difluoroethyl or 2,2,2-trichloroethyl).

Specific compounds of formula (I) are set out in the Tables below.

TABLE 1

| Compound No. | Ar | A |
| --- | --- | --- |
| 1 | 5-chloropyrid-3-yl | CH=CH |
| 2 | 5-methoxypyrid-3-yl | $CH_2$—$CH_2$ |
| 3 | 5-bromopyrid-3-yl | $CH_2$—$CH_2$ |
| 4 | 3,5-difluorophenyl | $CH_2$—$CH_2$ |
| 5 | 5-trifluoromethylpyrid-3-yl | CH=CH |
| 6 | 5-methoxypyrid-3-yl | CH=CH |
| 7 | 5-bromopyrid-3-yl | CH=CH |
| 8 | 3,5-difluorophenyl | CH=CH |
| 9 | 5-acetylenylpyrid-3-yl | $CH_2$—$CH_2$ |
| 10 | 5-acetylenylpyrid-3-yl | CH=CH |
| 11 | 5-cyanopyrid-3-yl | $CH_2$—$CH_2$ |
| 12 | 5-cyanopyrid-3-yl | CH=CH |
| 13 | 6-methoxypyrazin-2-yl | $CH_2$—$CH_2$ |
| 14 | 6-methoxypyrazin-2-yl | CH=CH |
| 15 | pyrid-3-yl | $CH_2$—$CH_2$ |
| 16 | pyrid-3-yl | CH=CH |
| 17 | 6-chloropyrazin-2-yl | $CH_2$—$CH_2$ |
| 18 | 6-chloropyrazin-2-yl | CH=CH |
| 19 | 3,5-dichlorophenyl | $CH_2$—$CH_2$ |
| 20 | 3,5-dichlorophenyl | CH=CH |

Compounds of formula (I) can be prepared by adapting methods described in the literature (such as WO 96/37494), by use of one or more of the following synthetic techniques described below and further illustrated in the Examples, or by combining literature methods with those methods described below. Throughout the following description R is alkyl (such as methyl) or phenylalkyl (such as benzyl).

A compound of formula (I) can be prepared by reacting a compound of formula (II) with formic acid at an elevated temperature (such as over 70° C.).

Alternatively, a compound of formula (I) can be prepared by reacting a compound of formula (II) with a suitable mixed formic anhydride (such as formic acetic anhydride).

A compound of formula (II) can be prepared by reacting a compound of formula (III) with a suitable chloroformate (such a vinyl chloroformate) and reacting the product so formed with a mineral acid (such as concentrated hydrochloric acid).

A compound of formula (III) can be prepared by treating a compound of formula (IV) first with a suitable base, such as lithium diisopropylamide (LDA) or lithium bis (trimethylsilyl)amide, and then reacting the product so formed with a compound ArHal, wherein Hal is a halogen.

A compound of formula (IV) can be prepared by reacting a compound of formula (V) with a compound of formula RL (wherein L is a suitable leaving group, such as a halide) preferably in the presence of a base.

Compounds of formula (V) can be prepared by processes analogous to those described in the art.

Compounds of formula (III) wherein A is CH=CH can be prepared by heating a compound of formula (III) wherein A is $CH_2CHZ$ (wherein Z is a suitable group, such as a thiono4-tolyloxy group) in a suitable solvent (such as xylene) at a suitable temperature (such as reflux).

Compounds of formula (III) wherein A is $CH_2CHZ$ (wherein Z is a suitable group, such as a thiono4-tolyloxy group) can be prepared by treating compounds of formula (III) wherein A is $CH_2CH(OH)$ with a suitable thionoformate (such as 4-tolyl chlorothiono formate) in the presence of a suitable base (such as NIN-dimethylaminopyridine).

Compounds of formula (III) wherein A is $CH_2CH(OH)$ can be prepared by acid hydrolysis of compounds of formula (III) wherein A is $CH_2CH(OZ')$ wherein Z' is a hydrolysable group (such as tert-butyldimethylsilyl).

A compound of formula (III) wherein A is $CH_2CH(OZ')$ wherein Z' is a hydrolysable group (such as tert-butyldimethylsilyl) can be prepared by reacting a corresponding compound of formula (IV) with a suitable base, such as lithium diispropylamide (LDA) or lithium bis (trimethylsilyl)amide, and reacting the product so formed with a compound ArHal, wherein Hal is a halogen.

A compound of formula (IV) wherein A is $CH_2CH(OZ')$ wherein Z' is a hydrolysable group (such as tert-butyldimethylsilyl) can be prepared by treating a corresponding compound of formula (VI) with tosylmethyl isocyanide (also known as (4-tolylsulfonyl)methylisocyanide) in the presence of a suitable base, such as potassium tert-butoxide.

A compound of formula (VI) wherein A is $CH_2CH(OZ')$ wherein Z' is a hydrolysable group (such as tert-butyldimethylsilyl) can be prepared by reacting a compound of formula (VI) wherein A is $CH_2CH(OH)$ with a compound Z'L wherein L is a leaving group.

A compound of formula (VI) wherein A is $CH_2CH(OH)$ can be prepared by reacting 2,5-dimethoxy-2,5-dihydrofuran, acetone dicarboxylic acid and an amine of formula $RNH_2$ (which is preferably in the form of a salt, such as a hydrochloride salt).

Alternatively a compound of formula (III) wherein A is CH=CH can be prepared by dehydrating a compound of formula (III) wherein A is $CH_2CH(OH)$ with a suitable dehydrating agent, such as diethylaminosulfurtrifluoride.

A compound of formula (III) wherein A is $CH_2CHF$ can be prepared by fluorinating a compound of formula (III) wherein A is $CH_2CH(OH)$ with, for example, a mixture of hydrogen fluoride and sulfur trifluoride.

A compound of formula (III) wherein A is $CH_2C(=O)$ can be prepared by reacting a compound of formula (III) wherein A is $CH_2CH(OH)$ with a suitable oxidising agent at a suitable temperature.

A compound of formula (III) wherein A is $CH_2CF_2$ can be prepared by fluorinating a compound of formula (III) wherein A is $CH_2C(=O)$ with, for example, diethylaminosulfurtrifluoride.

A compound of formula (III) wherein A is CH=CH can be prepared by reacting a compound of formula (III) wherein A is $CH_2CH(OZ')$, wherein Z' is a suitable group (such as $SO_2CH_3$) with a suitable amine (such as 1,8-diazabicyclo[5.4.0]undec-7-ene).

A compound of formula (III) wherein A is $CH_2CH(OZ')$, wherein Z' is a suitable group (such as $SO_2CH_3$) can be prepared by reacting a compound of formula (III) wherein A is $CH_2CH(OH)$ with a suitable acid chloride (such as mesyl chloride).

In further aspects the present invention provides processes for preparing compounds of formula (I) as hereinbefore described.

In a further aspect the invention provides a method of combating insect and like pests at a locus by applying to the locus or the pests an insecticidally effective amount of an insecticidal composition comprising a compound of formula (I) or an acid addition salt, quaternary ammonium salt or N-oxide derived therefrom.

The compounds of formula (I) can be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of formula (I) include: *Myzus persicae* (aphid), *Aphis iossvpii* (aphid), *Aphis fabae* (aphid), *Aedes aegypti* (mosquito), *Anopheles* spp. (mosquitos), *Culex* spp. (mosquitos), *Dysdercus fasciatus* (capsid), *Musca domestica* (housefly), *Pieris brassicae* (white butterfly), *Plutella xylostella* (diamond back moth), *Phaedon cochleariae* (mustard beetle), *Aonidiella* spp. (scale insects), *Trialeurodes* spp. (white flies), *Bemisia tabaci* (white fly), *Blattella germanica* (cockroach), *Periplaneta americana* (cockroach), *Blatta orientalis* (cockroach) *Spodoptera littoralis* (cotton leafworm), *Heliothis virescens* (tobacco budworm) *Chortiocetes terminifera* (locust), *Diabrotica* spp. (rootworms), *Aerotis* spp. (cutworms), *Chilo partellus* (maize stem borer), *Nilaparvata lugens* (planthopper), *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite), *Phyllcoptruta oleivora* (citrus rust mite), *Polyphagotarsonemus latus* (broad mite) and *Brevipalpus* spp. (mites). Further examples include insects which adversely affect the health of the public or of animals.

In order to apply the compounds of formula (I) to the locus of the nematode, insect or acarid pest, or to a plant susceptible to attack by the nematode, insect or acarid pest, the compound is usually formulated into a composition which includes in addition to a compound of formula (I) a suitable inert diluent or carrier material, and, optionally, a surface active agent. The amount of composition generally applied for the control of nematode pests gives a rate of active ingredient from 0.01 to 10 kg per hectare, preferably from 0.1 to 6 kg per hectare.

Thus in another aspect the present invention provides a insecticidal, acaricidal or nematicidal composition comprising an insecticidally, acaricidally or nematicidally effective amount of a compound of formula (I) and a suitable carrier or diluent therefor.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, Fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. In use, the concentrates are diluted in water and applied by means of a spray to the area to be treated.

Suitable liquid solvents for ECs include methyl ketones, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (TBFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl-naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or mnicrocapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of formula (I) may be the sole active ingredient of the composition or it may be admixed with one or more additional active ingredients such as insecticides, synergists, herbicides, fungicides or plant growth regulators where appropriate. Suitable additional active ingredients for inclusion in admixture with a compound of formula (I) may be compounds which will broaden the spectrum of activity of the compositions of the invention or increase their persistence in the location of the pest. They may synergise the activity of the compound of formula (I) or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-firylmethyl-(E)-(1R,3S)-2,2-dimethyl-3-(2-oxothiolan-3-ylidenemethyl)cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorfluazuron;

e) Organic tin compounds such as cyhexatin, fenbutatin oxide, azocyclotin;

f) Macrolides such as avermectins or milbemycins, for example such as abamectin, ivermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents;

k) Imidacloprid;

l) Spinosad.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compound of formula (I) to the other active ingredient in the composition will depend upon a number of factors including type of target, effect required from the mixture etc. However in general, the additional active ingredient of the composition will be applied at about the rate at which it is usually employed, or at a slightly lower rate if synergism occurs.

The invention is illustrated by the following Examples. Examples 1–4 illustrate the preparation of a range of compounds of formula (I). Examples 5 to 12 illustrate compositions suitable for the application of the compounds of formula (I) according to the invention. The following ingredients are referred to by their Registered Trade Marks and have the composition as shown below.

| Registered Trade Mark | Composition |
| --- | --- |
| Synperonic NP8 } | Nonylphenol-ethylene oxide |
| Synperonic NP13 } | condensate |
| Synperonic OP10 } | |
| Aromasol H | Alkylbenzene solvent |
| Solvesso 200 | Inert organic diluent |
| Keltrol | Polysaccharide |

Selected NMR data and melting point data are presented in the Examples. For NMR data, no attempt has been made to list every absorption. The following abbreviations are used throughout the Examples:

| | | | |
| --- | --- | --- | --- |
| mp = | melting point (uncorrected) | ppm = | parts per million |
| s = | singlet | t = | triplet |
| d = | doublet | q = | quartet |
| dd = | double doublet | brd = | broad doublet |
| m = | multiplet | | |

EXAMPLE 1

This Example illustrates the preparation of exo-3-(5-chloropyrid-3-yl)-endo-3-cyano-8-formyl-8-azabicyclo[3.2.1]oct-6-ene (Compound No. 1 I).

Stage 1

2,5-Dimethoxy-2,5-dihydrofuran (97.5 g) was dissolved in water (650 ml) and treated with aqueous hydrochloric acid (3.75 ml, 2M) under an atmosphere of nitrogen. The mixture was heated to 96° C. with stirring and aqueous methanol (about 100 ml) distilled from the reaction vessel until the reaction solution reached 98–99° C. The reaction was cooled to ambient temperature, acetone dicarboxylic acid (146 g) added in one portion followed by a solution of sodium hydrogen phosphate (53.25 g) and sodium hydroxide (15.0 g) in water (500 ml). 1,4-Dioxane (100 ml) was added and a solution of benzylamine hydrochloride (71.75 g) in water (330 ml) added dropwise over 10 minutes. The mixture was rapidly stirred for a further 4 hours, acidified with aqueous hydrochloric acid (2M), dichloromethane (500 ml) added and the reaction mixture stirred for 10 minutes. The aqueous phase was decanted from the residual brown gum, filtered through a bed of kieselguhr and the filtrate extracted with dichloromethane (3×500 ml). The aqueous phase was collected, basified with potassium carbonate and extracted with ethyl acetate (3×1000 ml). The organic fractions were combined, dried (magnesium sulfate) and evaporated under reduced pressure to give a brown oil, 55 g, containing a mixture of exo- and endo- 6-hydroxy-8-benzyl-8-azabicyclo[3.2.1]octan-3-one (ratio 7:1).

Stage 2 tert-Butyldimethylsilyl chloride (26.5 g) was dissolved in N,N-dimethylformamide (400 ml, dry) with stirring under an atmosphere of nitrogen and imidazole (25.0 g) added in portions. The mixture was stirred for 10 minutes and a solution of the product from Stage 1 (55 g) in N N-dimethylfonnamide (250 ml, dry) added in portions. The dark brown reaction mixture was stirred at ambient temperature for 3 hours, stored for 18 hours and poured into water (2,500 ml). The product was extracted into hexane (3×800 ml), the combined organic phases washed with water (2×1000 ml) and dried (sodium sulfate). The solvent was evaporated under reduced pressure to give a brown oil, 44.5 g, containing a mixture of exo- and endo-6-tertbutyldimethylsilyloxy-8-benzyl-8-azabicyclo[3.2.1]octan-3-one (ratio 7:1).

Stage 3

The material from Stage 2 (44 g) in 1,2-dimethoxyethane (160 ml, dry) containing 4-tolylsulfonylmethylisocyanide (41 g) was added dropwise over 1.5 hours to a mixture of potassium tert-butoxide (19.0 g) and sodium ethoxide (14.5 g) in 1,2-dimethoxyethane (140 ml, dry) at 40° C. under an atmosphere of nitrogen. The mixture was stirred for 1 hour at 40° C. and allowed to cool to ambient temperature and stirred for a further 18 hour. The mixture was poured into water (1,500 ml), extracted with hexane (2×750 ml), and the combined organic phases washed with water (400 ml) and dried (sodium sulfate). The solvent was evaporated under reduced pressure to give a brown gum, 39.7 g, containing a mixture of exo- and endo- 6-tert-butyldimethylsilyloxy-8-benzyl-exo-3-cyano-8-azabicyclo[3.2.1]octane (ratio 7:1)

Stage 4

The product from Stage 3 (15.0 g) was dissolved in dry tetrahydrofuran (100 ml) containing 3,5-dichloropyridine (4.30 g) at 0° C. under an atmosphere of nitrogen with stirring. Lithium bis-(trimethylsilyl) amide (38.0 ml of a tetrahydrofuran solution, 1M) was added dropwise to the solution over 1 hour, maintaining the reaction temperature below 5° C. The reaction was allowed to warm to ambient temperature and stirred for 18 hours. The reaction mixture was treated with further lithium bis-(trimethylsilyl)amide (7.0 ml of a tetrahydrofuran solution, 1M) added dropwise over 2 hours at ambient temperature, stirred for 6 hours and stored for 18 hours. The mixture was poured into water (500 ml), extracted with hexane (2×400 ml), the combined organic phase was washed with water, dried (sodium sulfate) and evaporated under reduced pressure to give a brown oil, 18.5 g. The oil was fractionated by chromatography (silica, hexane/ethyl acetate 10:1 by volume) to give 8-benzyl-exo-6-tert-butyldimethylsilyloxyxo-3-(5-chloropyrid-3-yl)-endo-3-cyano-8-azabicyclo[3.2.1]octane, yellow oil, 7.8 g.

$^1$H NMR (CDCl$_3$): δ0.15(6H,two s); 0.90(9H,s); 2.19–2.40(5H,m); 2.80–2.90 (1H,q); 3.30(1H,m); 3.60(1H,m); 3.90–4.10(2H,q); 5.05(1H,dd); 7.20–7.45(5H,m); 7.80(1H,t); 8.55(1H,d); 8.70(1H,d)ppm.

Stage 5

The product from Stage 4 (4.92 g) was dissolved in tetrahydrofuran (20 ml) with stirring, aqueous hydrochloric acid (30 ml, 4M) added and the mixture stirred at ambient temperature for 18 hours and stored for 3 days. The mixture was diluted with water, extracted with ethyl acetate (three times) and the acidic aqueous phase separated and basified with sodium carbonate. The aqueous basic phase was extracted with dichloromethane (three times), dried (magnesium sulfate) and evaporated under reduced pressure to give exo-3-(5-chloropyrid-3-yl)-endo-3-cyano-exo-6-hydroxy-8-benzyl-8-azabicyclo[3.2.1]octane as an off-white solid, 2.71 g, mp 162.5–164.5° C.

$^1$H NMR (CDCl$_3$): δ2.00(1H,d); 2.10–2.40(4H,m); 2.95 (1H,q); 3.40(1H,m); 3.60(1H,m); 4.00(2H,q); 5.05(1H,m); 7.20–7.40(5H,m); 7.85(1H,t); 8.55(1H,d); 8.70(1H,d)ppm.

Stage 6

The product from Stage 5 (2.61 g) was suspended in dichloromethane (30 ml) containing 4-dimethylaminopyridine (0.99 g) with stirring at ambient temperature. 4-Tolyl chlorothionoformate (1.25 ml) was added dropwise and the reaction mixture stirred at ambient temperature for 18 hours. The mixture was poured into water, extracted with dichloromethane (three times), the combined organic phase dried (magnesium sulfate) and evaporated under reduced pressure to give a brown oil containing exo-3 -(5-chloropyrid-3-yl)-endo-3-cyano-exo-6-(thiono-4-tolyloxy)-8-benzyl-8-azabicyclo[3.2.1]octane, which was used in Stage 7 without further purification.

Stage 7

The product from Stage 6 (4.5 g) was dissolved in xylene (40 ml, dry) and heated to 160° C. for 18 hours under an atmosphere of nitrogen with stirring. The reaction was cooled to ambient temperature, treated with aqueous hydrochloric acid (2M) until strongly acidic and extracted with ethyl acetate (three times). The aqueous acidic phase was separated, basified with sodium carbonate, extracted with ethyl acetate (three times) and the organic phases combined and dried (magnesium sulfate). The solvent was evaporated under reduced pressure to give the required product as an off-white solid, 2.20 g. A portion, (0.2 g), was fractionated by thick layer chromatography (silica; hexane/ethyl acetate 1:1 by volume) to give an analytically pure sample of exo-3-(5-chloropyrid-3-yl)-ndo-3-cyano-8-benzyl-8-azabicyclo [3.2.1]oct-6-ene, (0.15 g), colourless solid, mp 130–1° C.

$^1$H NMR (CDCl$_3$): δ2.20–2.40(4H,m); 3.60(2H,s); 3.75 (2H,m); 6.30(2H,s); 7.20–7.40(5H,m); 7.85(1H,t); 8.55(1H, d); 8.75(1H,d)ppm.

Stage 8

Acetic-formic mixed anhydride (prepared from acetic anhydride and sodium formate) was added to the product from Stage 7 (0.10 g) dissolved in dichloromethane (2 ml, dry) containing N,N-diisopropylethylamine (0.078 ml) and the mixture stirred at ambient temperature for 2 hours. The mixture was poured into a solution of aqueous sodium carbonate (20 ml), extracted with ethyl acetate (2×20 ml). The organic extracts were combined, dried (magnesium sulfate) and evaporated under reduced pressure to give the required product as a colourless solid, mp 151–4° C.

$^1$H NMR (CDCl$_3$): δ2.15–2.50(4H,m); 4.75(1H,m); 5.20 (1H,m); 6.50(2H,s); 7.80(1H,t); 8.30(1H,d); 8.45(1H,brd); 8.55(1H,brd)ppm.

EXAMPLE 2

This Example illustrates the preparation of exo-3-(5-methoxypyrid-3-yl)endo-3-cyano-8-formyl-8-azabicyclo [3.2.1]octane (Compound No. 2 Table I).

exo-3-(5-Methoxypyrid-3-yl)-endo-3-cyano-8-azabicyclo[3.2.1]octane (0.05 g) was added to 90% fornic acid (1 ml) and the mixture heated at 110° C. for 24 hours. After cooling to room temperature the mixture was evaporated under reduced pressure, toluene (2×5 ml) added and the mixture evaporated under reduced pressure. The mixture was added to 100% formic acid (2 ml) and heated at 90° C. for 18 hours. The mixture was then evaporated under reduced pressure, dilute sodium carbonate (0.5 ml) added and the mixture extracted with ethyl acetate (×2). The combined extracts were evaporated under reduced pressure and preparative thin layer chromatographed [SiO$_2$; ethyl acetate:methanol (90:10)] to give exo-3-(5-methoxypyrid-3-yl)-endo-3-cyano-8-formyl-8-azabicyclo[3.2.1]octane (0.006 g) mp 134–136° C.

$^1$H NMR (270 MHz) CDCl$_3$: δ8.35 (1H, d), 8.30(1H,d), 8.20(1H,s), 7.25(1H,t), 4.85(1H,m), 4.30(1H,m), 3.90(3H,s) and 2.6–2.1(8H,m)ppm.

EXAMPLE 3

This Example illustrates the preparation of exo-3-(5-bromopyrid-3-yl)-endo-3-cyano -8-formyl-8-azabicyclo [3.2.1]octane (Compound No. 3 Table I).

Vinyl chloroformate (4.2 ml) was added to exo-3-(5-bromopyrid-3-yl)-endo-3-cyano -8-methyl-8-azabicyclo

[3.2.1]octane (5.0 g) in dry tetrahydrofuran (50 ml) at 0° C. The mixture was refluxed for 3 hours and allowed to stand at room temperature overnight. Water and ethyl acetate were added and the organic phase separated, washed with saturated sodium bicarbonate, dried (MgSO$_4$) and evaporated under reduced pressure to give exo-3-(5-bromopyrid-3-yl)-endo-3-cyano-8-(vinyloxycarbonyl)-8-azabicyclo[3.2.1]octane (6.2 g, not pure) mp 63–66° C.

Concentrated hydrochloric acid (5 ml) was added to a mixture of exo-3-(5-bromopyrid-3-yl)- endo-3-cyano-8-(vinyloxycarbonyl)-8-azabicyclo[3.2.1]octane (4.08 g) in methanol (100 ml). The mixture was refluxed for 1 hour, allowed to stand at room temperature for 18 hours and evaporated under reduced pressure. Acid/base extraction gave exo-3-(5-bromopyrid-3-yl)-endo-3-cyano-8-azabicyclo[3.2.1]octane (2.77 g) mp 135–137° C.

Formic acetic anhydride (0.4 g) was added dropwise to a stirred solution of exo-3-(5-bromopyrid-3-yl)-endo-3-cyano-8-azabicyclo[3.2.1]octane (0.52 g) in diethyl ether (400 ml) at room temperature. After 30 minutes the mixture was evaporated under reduced pressure to a volume of approximately 100 ml at which point a precipitate formed which was filtered to give exo-3-(5-bromopyrid-3-yl)-endo-3-cyano-8-formyl-8-azabicyclo[3.2.1]octane (0.295 g) mp 146–148° C.

$^1$H NMR (270 MHz) CDCl$_3$: δ8.65(2H,m), 8.19(1H,s), 7.89(1H,t), 4.86 (1H,m), 4.32(1H,m) and 2.6–2.1(8H,m) ppm.

EXAMPLE 4

This Example illustrates the preparation of exo-3-(3,5-difluorophenyl)-endo-3-cyano -8-formyl-8-azabicyclo[3.2.1]octane (Compound No. 4 Table I).

Vinyl chloroformate (2.8 ml) in tetrahydrofuran (10 ml) was added dropwise to a solution of exo-3-(3,5-difluorophenyl)-endo-3-cyano-8-methyl-8-azabicyclo[3.2.1]octane (5.7 g) in tetrahydrofuran (25 ml) at 0° C. under nitrogen. The mixture was heated at 50° C. for 3 hours and then cooled and filtered. The filtrate was washed with brine, dried (MgSO$_4$) and evaporated under reduced pressure to give exo-3-(3,5-difluorophenyl)-endo-3-cyano-8-(vinyloxycarbonyl)-8-azabicyclo[3.2. 1]octane (5.7 g).

exo-3-(3,5-Difluorophenyl)- endo-3-cyano-8-(vinyloxycarbonyl)-8-azabicyclo[3.2.1]octane (5.7 g) and concentrated hydrochloric acid (5 m) were heated under reflux in methanol (70 ml) for 4 hours. The mixture was then cooled to room temperature, basified with 2M sodium hydroxide and extracted with dichloromethane. The combined extracts were washed with brine, dried (MgSO$_4$) and evaporated under reduced pressure. Chromatography [SiO$_2$; dichloromethane:methanol (90:10)] gave exo-3-(3,5-difluorophenyl)-endo-3-cyano-8-azabicyclo[3.2.1]octane (2.85 g) mp 112° C.

Formic acetic anhydride (0.46 g) was added dropwise to a stirred solution of exo3-(3,5-difluorophenyl)-endo-3-cyano-8-azabicyclo[3.2.1]octane (0.516 g) in diethyl ether (35 ml) at room temperature under nitrogen. After 20 minutes the mixture was allowed to stand overnight and then filtered. The filtrate was slowly evaporated and a precipitate formed. Filtration gave exo-3-(3,5-difluorophenyl)-endo-3-cyano-8-formyl-8-azabicyclo[3.2.1]octane (0.22 g) mp 146° C.

$^1$H NMR (270 MHz) CDCl$_3$: δ8.19(1H,s), 7.00(2H,m), 6.79(1H,m), 4.82(1H,m), 4.30(1H,m) and 2.6–2.1(8H,m) ppm.

EXAMPLE 5

This Example illustrates an emulsifiable concentrate composition which is readily convertible by dilution with water into a liquid preparation suitable for spraying purposes. The concentrate has the following composition:

|  | % Weight |
|---|---|
| Compound No. 1 | 25.5 |
| SYNPERONIC NP13 | 2.5 |
| Calcium dodecylbenzenenesulphonate | 2.5 |
| AROMASOL H | 70 |

EXAMPLE 6

This Example illustrates a wettable powder composition which is readily convertible by dilution with water into a liquid preparation suitable for spraying purposes. The wettable powder has the following composition:

|  | % Weight |
|---|---|
| Compound No. 1 | 25.0 |
| Silica | 25.0 |
| Sodium lignosulphonate | 5.0 |
| Sodium lauryl sulphate | 2.0 |
| Kaolinite | 43.0 |

EXAMPLE 7

This Example illustrates a dusting powder which may be applied directly to plants or other surfaces and comprises 1% by weight of Compound No. 2 and 99% by weight of talc.

EXAMPLE 8

This Example illustrates a concentrated liquid formulation suitable for application by ultra low volume techniques after mixing with paraffinic diluents.

|  | % Weight |
|---|---|
| Compound No. 2 | 90.0 |
| SOLVESSO 200 | 10.0 |

EXAMPLE 9

This Example illustrates a capsule suspension concentrate which is readily convertible by dilution with water to form a preparation suitable for application as an aqueous spray.

|  | % Weight |
|---|---|
| Compound No. 3 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 10

A ready for use granular formulation:

| | % Weight |
|---|---|
| Compound No. 4 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 11

An aqueous suspension concentrate:

| | % Weight |
|---|---|
| Compound No 4 | 5.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 12

This Example illustrates a water dispersible granule formulation.

| | % Weight |
|---|---|
| Compound No. 2 | 5 |
| Silica | 5 |
| Sodium lignosulphate | 10 |
| Sodium dioctylsulphosuccinate | 5 |
| Sodium acetate | 10 |
| Montmorillonite powder | 65 |

EXAMPLE 13

This Example illustrates the insecticidal properties of the compounds of formula (I). The activity of the compounds of formula (I) was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYNPERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus Mersicae*) are presented below. The results indicate a grading of mortality (score) designated as A, B or C wherein C indicates less than 40% mortality, B indicates 40–79% mortality and A indicates 80–100% mortality. In this test Chinese cabbage leaves were infested with aphids, the infested leaves were sprayed with the test composition, and the mortality assessed after 3 days. Compound Nos. 1, 2 and 3 of Table I and gave a mortality score of A.

The formula referred to hereinabove are set out as follows

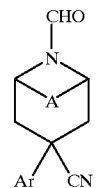
(I)

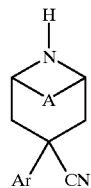
(II)

(III)

(IV)

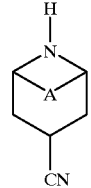
(V)

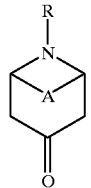
(VI)

What is claimed is:

1. A compound of formula (I):

(I)

wherein A is $CH_2-CH_2$ or $CH=CH$; and Ar is pyridinyl optionally substituted with cyano, alkyl, alkenyl, alkynyl or alkoxy; or an acid addition salt, quaternary ammonium salt or N-oxide derived therefrom.

2. A compound of formula (I) as claimed in claim 1 wherein A is $CH=CH$.

3. A compound according to claim 1 wherein Ar is pyridinyl optionally substituted with cyano, $C_{1-4}$ alkyl, $C_{2-4}$ alkenyl, $C_{2-4}$ alkynyl or $C_{1-4}$ alkoxy.

4. A compound according to claim 1 wherein Ar is pyridinyl optionally substituted with cyano, $C_{1-4}$ alkyl, $C_{2-4}$ alkynyl or $C_{1-4}$ alkoxy.

5. A compound according to claim 1 wherein Ar is 3-pyridinyl optionally substituted at the 5-position with $C_{1-4}$ alkyl, $C_{2-4}$ alkynyl or $C_{1-4}$ alkoxy.

6. An insecticidal, acaricidal or nematicidal composition comprising an insecticidally, acaricidally or nematicidally effective amount of a compound of formula (I) according to claim 1, and a suitable carrier or diluent therefore.

7. A method of combating and controlling insect, acarine or nematode pests at a locus which comprises treating the pests or the locus of the pests with an effective amount of a compound according to claim 1.

8. A method according to claim 7 wherein the pests are insect pests of growing plants.

9. A process for preparing a compound of formula (I) as claimed in claim 1 comprising reacting a compound of formula (II):

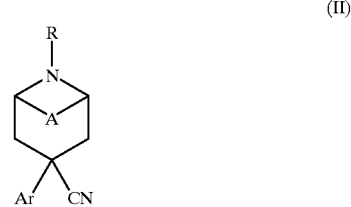

(II)

with either formic acid at an elevated temperature or with a mixed formic anhydride.

10. A method of combating and controlling insect, acarine or nematode pests at a locus which comprises treating the pests or the locus of the pests with an effective amount of a composition according to claim 6.

* * * * *